United States Patent

Walker et al.

[11] B 3,982,177
[45] Sept. 21, 1976

[54] SOIL SAMPLE CONDUCTIVITY MEASUREMENT UTILIZING A BRIDGE CIRCUIT AND PLURAL ELECTRODE CELL

[75] Inventors: John W. Walker, Belmar; Douglas C. Pearce, Sea Girt, both of N.J.

[73] Assignee: The United States of America as represented by the Secretary of the Army, Washington, D.C.

[22] Filed: Oct. 8, 1970

[21] Appl. No.: 79,099

[44] Published under the second Trial Voluntary Protest Program on January 13, 1976 as document No. B 79,099.

[52] U.S. Cl. ............................. 324/13; 324/30 B
[51] Int. Cl.² .................. G01V 3/06; G01N 27/04; G01R 27/00
[58] Field of Search ................. 324/13, 14, 30 B, 65

[56] References Cited
UNITED STATES PATENTS

| | | | |
|---|---|---|---|
| 2,583,284 | 1/1952 | Wyllie et al.......................... | 324/13 X |
| 2,613,250 | 10/1952 | Bilhartz et al. .................... | 324/13 X |
| 2,875,401 | 2/1959 | Owen.................................... | 324/13 |
| 2,914,725 | 11/1959 | Carter et al............................ | 324/30 |

*Primary Examiner*—Gerard R. Strecker
*Attorney, Agent, or Firm*—Nathan Edelberg; Jeremiah G. Murray; Daniel Sharp

[57] ABSTRACT

A method of measuring at low frequency the electrical conductivity of a heterogeneous soil sample contained in an electrically insulating soil container or cell having at least two, or a colinear array of three or more, chemically inert probes or electrodes wherein the soil cell first is calibrated using a standard solution of known conductivity to obtain a cell constant k for each pair of probes. The cell constant for a given pair of probes is the product of the resistance measured between said pair of probes and the known conductivity of the solution. This cell constant is representative of the factor $1/a$ in a formula for resistance $R = \rho \, l/a$ of a material where $\rho$ is the resistivity of the material between adjacent probes, $l$ is the length of the material — substantially equal to the probe spacing — and $a$ is the cross-sectional area of the material through which the current flows between the pair of probes under consideration. The cell constant thus obtained is applied to subsequent soil measurements for any number of such soil samples. The solution now is emptied from the cell. The cell is then filled with a soil sample and the resistance of various combinations of two-terminal networks, each including a pair of probes and the soil disposed therebetween, is measured. The resistance of the soil measured between a given pair of probes is divided by the aforesaid cell constant for that pair of probes to determine the conductivity of the soil disposed between said pair of probes without having to measure the size and shape of either the soil cell or the heterogeneous soil sample contained therein.

2 Claims, 3 Drawing Figures

INVENTORS,
JOHN W. WALKER &
DOUGLAS C. PEARCE

SOIL SAMPLE CONDUCTIVITY MEASUREMENT UTILIZING A BRIDGE CIRCUIT AND PLURAL ELECTRODE CELL

BACKGROUND OF THE INVENTION

In making geophysical surveys and in deployment of various electronic surveillance and detection devices which interface with the ground and in the selection of antenna sites for communication systems, an accurate determination of the resistivity — or its reciprocal — the conductivity — of localized samples of soil is often necessary.

Although there are several reliable laboratory techniques for measurement of the electromagnetic parameters of lossy dielectric media, they are, by nature of their instrumentation, wholly unsuited for use outside of the laboratory. Devices that are designed for use in the field, such as those employing the wave-tilt or polarization anomaly technique, lack the selectivity of the sample measuring devices of the laboratory. Both the wave-tilt and polarization anomaly techniques are integrating methods which measure the bulk conductivity of the earth. In these methods, there is some inherent weighting of the measurements toward the material directly beneath the device; however, the data is strongly influenced by all of the surrounding earth, as well as by local topography. Several methods of measuring the characteristics of soil use an array of probes placed in situ in the soil and thus involve an unconfined soil sample. With such a large unconfined sample one has to deal with a so-called infinite halfspace, roughly the shape of a hemisphere for a single probe and more or less dumb-bell shaped for two probes. Not only are the current paths involved in such an infinite halfspace many and complex, but departure from homogeneity in this halfspace (practically always the case) will distort the equivalent space and cause severe errors in interpretation. Furthermore, measurements for such an unconfined sample can only be a mean value not at all representative of localized regions within that relatively large halfspace.

Obviously, the integrating features of these techniques would be of some value where the gross conductivity of the earth is of importance. However, these devices would be equally ill-suited for the task of sorting out the individual characteristics of each soil occurring within a particular site. It is also important to note that these latter devices are generally restricted to measurements at frequencies in the low megahertz range and that a high to medium power signal source is required. Both of these features tend to limit application of these techniques to the communications field.

SUMMARY OF THE INVENTION

In accordance with the invention, the resistivity of a relatively small confined sample of soil taken from some particular local region of interest in the field can be measured. One of the problems with prior techniques for laboratory type measurement of soil conductivity is that a calculation is necessarily based on the geometry of the sample, since the ratio of the length and the cross-sectional area of the sample and resistance of the material must both be known. The calculation of the ratio of length and cross-sectional area can be quite difficult, particularly if the sample is confined within a complex geometrical structure. In practice, the soil-confining means should be free from corners and other abrupt changes in shape, such as would occur with enclosures having such well known simple geometrical configurations as cylinders, prisms, parallelopipeds, etc., in order to allow proper packing and easy removal of the soil sample after test. It has been found that soil cannot be packed smoothly into sharp corners without air spaces being formed and it is difficult also to remove the soil sample from these sharp corners of a container after completion of the test. In accordance with the invention, a soil test cell is used in which the configuration of the soil-containing channel is free of sharp discontinuities and may, for example, be a U-shaped channel with rounded edges such as found in the ordinary household bathtub. With such a configuration for the soil cell, the calculations of the geometric factors are highly impractical, as in the case of containers of regular geometrical configuration. Instead, the soil cell is first calibrated with a fluid medium of known conductivity which completely fills the cell. An example of such a fluid is an aqueous solution of potassium chloride which, depending upon the concentration and temperature, has a known conductivity. The soil cell also includes a cover, which fits over the base and contains three probes which protrude into the liquid medium and which extend outside the cover to allow connection to be made to a resistance measuring device. A switch is provided to connect different pairs of probes, if more than one pair is used, to the resistance measuring device, which can be a conventional wheatstone bridge. The resistance between each combination of pairs of probes is measured by the wheatstone bridge. The cell constant $k$ for each said pair of probes then can be calculated as the ratio of the measured resistance between that pair of probes and the conductivity of the solution. The cell constant thus obtained is applied to all subsequent soil measurements.

The cell having thus been calibrated and emptied of the calibrating fluid, the soil sample under test, after necessary preparation, is packed into the U-shaped channel formed in the base of the soil cell. The cell cover in which the fixedly mounted probes are mounted, then is placed over the base of the probes extended to the soil sample. The probes terminate outside the cover and are available for connection to the resistance measuring device. The resistance between each pair of probes is measured and the ratio of this measurement for that pair of probes to the cell constant for the same pair of probes defines the conductivity of the soil sample disposed between the corresponding pair of probes. If more than one pair of probes is used, the average of the values of soil conductivity for the various pairs is used. The averaging of conductivity measurements are made for more than one pair of probes permits a more meaningful measurement to be made since soil, no matter how well mixed and prepared prior to placement in the soil cell, tends to be a rather heterogeneous medium.

DETAILED DESCRIPTION OF THE PREFERRED EMBODIMENT

Figure 1:
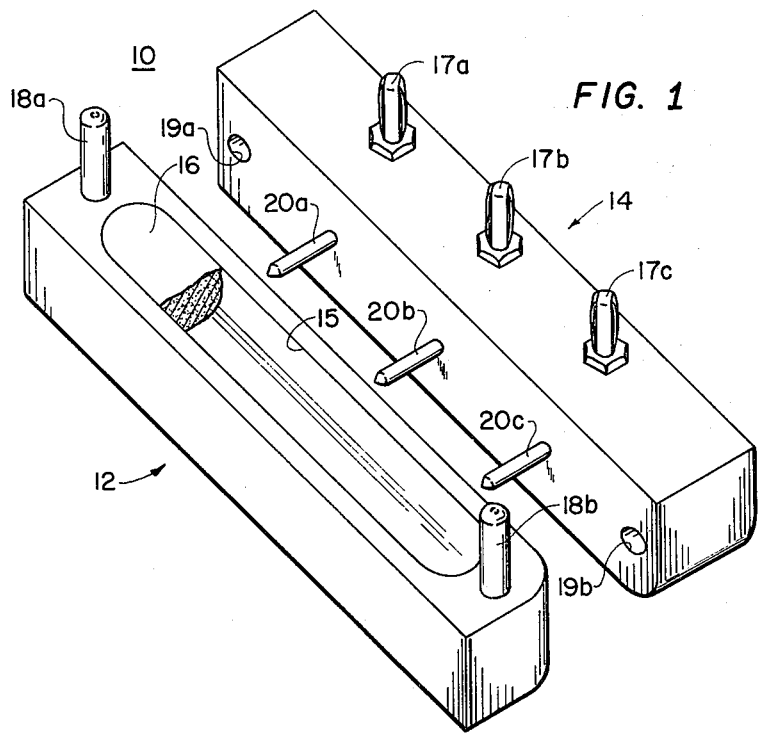
FIG. 1 is a view showing the two mating portions of a typical soil cell for use of the invention.
Figure 2:
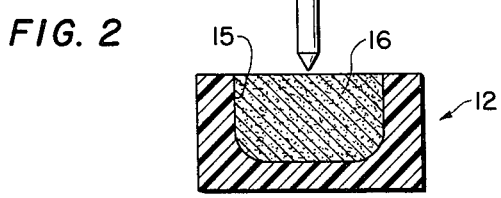
FIG. 2 is a view showing details of the probe-contact assembly used in the soil cell cover of FIG. 2.

Referring to FIG. 1 of the drawing, two mating portions 12 and 14 of a soil cell 10 are shown disassembled. The cell body 12 is machined from a plastic, such as a polycarbonate thermoplastic, which is durable, rigid, and easily cleaned of soil particles. The cell body or base 12 of the soil cell contains a U-shaped channel 15 into which the soil sample 16 is packed. The channel 15 has rounded ends so as to eliminate corners and thereby facilitate cleaning of the cell and also to provide the proper packing of the soil. The cell cover 14 contains a plurality of probes 20a, 20b and 20c which are adapted to penetrate into the soil sample contained within the channel 15 of the cell body 12. The probes 20 may be bent at right angles, as shown in FIG. 2, so as to permit necessary external electrical connections to be made thereto. The probes 20 are firmly mounted in the cell cover block 14 and, in the example shown in FIGS. 1 and 2, are connected to banana type plugs 17a to 17c placed in the side of the cover block normal to the probes 20. The probes 20 can be threaded at one end to engage a threaded aperture in the corresponding plug 17, as indicated in FIG. 2. The probes 20 may, alternatively, be continuous members bent at right angles and molded into the plastic cover. The use of banana plugs 17, however, permits the necessary external electrical connections to be made conveniently. Furthermore, the use of right-angle mounted plugs eliminate the need for lead connections to the cell since the entire soil cell assembly 10 can be plugged into a socket in the measuring bridge 25 shown schematically in FIG. 3. After assembly of the two portions of the probe-plug assembly, the entire probe-plug assembly can be molded into the plastic cover 14.

Two guide pins 18a and 18b, which may be made of stainless steel, are located near the end of the cell base 12 and are aligned with corresponding apertures 19a and 19b in the cell cover 14. These guide pins 18, which may be molded into the base 12, assure that the probes 20 enter the packed soil sample perpendicularly without wobble and in the proper alignment with respect to one another. This arrangement prevents enlarged holes about the probes 20 and abnormally high contact resistance at the probe-to-soil interface.

The dimensions of the soil cell 10 generally are not critical. The electrode or probe spacing is consistent with the overall length of the soil cell, with the center probe, in the case of an odd number of probes, being located at the midpoint of the U-shaped channel 15 and the end electrodes placed at some convenient distance from the end of the channel 15 with respect to the radius of curvature of the channel. The length-to-diameter ratio of this soil channel 15 should be maintained at a suitable value which can be of the order of 10 to 1. With this symmetrical configuration, the resistance between probe pairs 20a and 20b and 20b and 20c should be approximately the same and the resistance between electrode pairs 20a and 20c should be approximately twice that of the resistance between the aforesaid adjacent pairs.

The soil cell 10 must be calibrated with a material of known conductivity and, inasmuch as solutions are convenient materials for such purpose, the two halves of the soil cell should form a relatively fluid-tight test unit.

Figure 3:
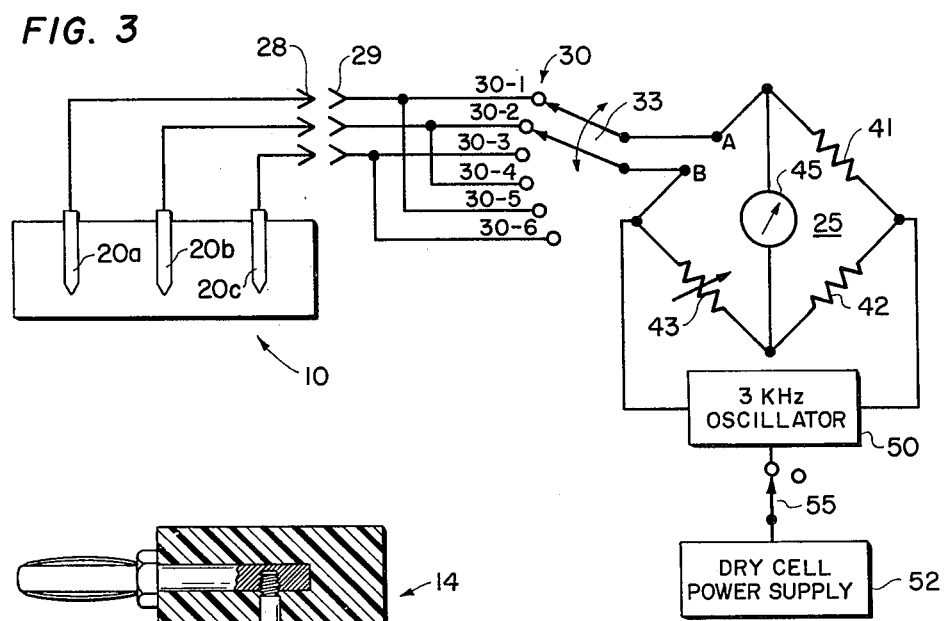
FIG. 3 is a schematic diagram of a typical circuit used for measuring the conductivity of soil disposed within the soil cell.

Although a colinear three-electrode cell is shown in FIGS. 1 to 3 the invention is not restricted to that number of electrodes. For example, any number of probes in excess of two can be used. For simplicity of the interpretation of the results, the electrodes should be in colinear array.

Before making soil conductivity tests with the circuit shown in FIG. 3, it is necessary first to calibrate the cell 10. This is done by inserting an aqueous solution of a well known material, such as potassium chloride which has a known conductivity $\sigma'$. In practice, this is accomplished by placing the solution in a well known chem cell having a known cell constant k. The electrodes of this standard cell are connected to a resistance bridge supplied with the frequency at which the conductivity of the soil sample is to be later measured. By dividing the cell constant k by the value R' of resistance measured between the electrodes of the standard cell when it is filled with the solution in question, the conductivity $\sigma'$ of the solution is determined. The solution of known conductivity $\sigma'$ now is poured out of the standard cell and into the channel 15 in the cell base 12 and the cover 14 is placed over this cell base 12. Each combination of two probes 20 now is connected by way of a switch 30 into terminals A and B of the resistive bridge 25, indicated schematically in FIG. 3. For simplicity, the probes 20a, 20b and 20c are indicated in FIG. 3 as extending through the top of the cell 10 and as being connected by leads to corresponding male connector 31 which engage the corresponding female connector 32; actually, the probes terminate in banana-type plugs 17, which correspond to the connectors 31 and plug into a socket mounted in the bridge housing, not shown, which socket corresponds to the connector 32. The switch 30 includes six contacts 30-1, 30-2, ... 30-6. The contacts 30-1 and 30-2 are connected to probes 20a and 20b, respectively, contacts 30-3 and 30-4 connect to respective probes 20b and 20c and contacts 30-5 and 30-6 connect to respective probes 20a and 20c. When the rotary arms 33 of the double pole switch 30 engages contacts 30-1 and 30-2, the probes 20a and 20b are connected to points A and B in the unknown resistance arms of the resistance measuring device 25. The latter is indicated in FIG. 3 as a conventional Wheatstone bridge having a matched pair of resistors 41 and 42 of known value and a variable decade resistor 43, which may have a direct digital readout. A null detector 45 is provided in one diagonal of the bridge 25 and a source of low frequency current of about 3KHz is connected in the other bridge diagonal. The current source may consist of an audio frequency oscillator 50 driven by a low voltage direct current source 52, such as a 1.5 volt dry cell. With the switch arm 33 engaging contacts 30-1 and 30-2, the resistance $R_{ab}'$ between probes 20a and 20b is measured and the cell constant $k_{ab}$ for that pair of probes is given by the product of this measured resistance and the known conductivity $\sigma'$ of the solution. The switch arm 33 is now moved to engage contacts 30-3 and 30-4 and the resistance $R_{bc}'$ between probes 20b and 20c is measured. The cell constant $K_{bc}$ for the probe pair 20b and 20c is calculated by multiplying the measured resistance $R_{ab}'$ and the known conductivity $\sigma'$ of the solution. Similarly, with the switch arm 33 moved to engage contacts 30-5 and 30-6, the resistance $R_{ac}'$ between probes 20a and 20c is measured and the cell constant $k_{ac}$ for the probe pair 20a and 20c is given by the product of $\sigma'$ and $R_{ac}'$. The cell constants $k_{ab}$, $k_{bc}$ and $k_{ac}$ are a function of the ratio of the length 1 to the cross-sectional area a in the resistance formula $R = \rho l/a$ for the region between the corresponding electrodes. The cell constant is independent of the resistivity $\rho$ of the material but does vary with frequency, although not appreciably for small frequency changes.

Consequently, the calibration of the cell should be made with substantially the same frequency as used for actual soil conductivity measurements.

Having determined the cell constants and removing the calibrating solution, it is now possible to determine the conductivity of the soil sample which can be packed by hand into the cell channel 15 of cell body 12 with just enough pressure to assure that the sample is firmly seated in the channel and that the density of packing roughly approximates the field density for moist soil. The soil first is stirred slightly to give a representative distribution of soil particles if separation has occurred and disintegrate any clods, if necessary. In some cases, it may be essential to add demineralized water to the sample if the soil has dried out materially and to stir vigorously until distribution of moisture throughout the sample is uniform. An excess of soil above the top of the channel is desirable so that the packed sample can be leveled off flush with the top of the channel by a spatula or similar device. The block cover 14 of the cell 10 is placed over the guide pins 18 and the cell is closed with a firm, continuous pressure on the cover 14 which brings the probes 20 in contact with the soil 16. The cell 10 then is placed in the socket of the bridge and the oscillator 50 is activated by closure of the switch 55.

With the rotary arm 33 of switch 30 engaging contacts 30-1 and 30-2, the resistance $R_{ab}$ of the soil sample disposed between probes 20a and 20b is measured. Similarly, with the arm 33 engaging contacts 30-3 and 30-4, the resistance $R_{bc}$ of the soil sample bounded by probes 20b and 20c is measured. Finally, with the arm 33 engaging contacts 30-5 and 30-6, the resistance $R_{ac}$ of the soil sample 16 disposed between the probes 20a and 20c is measured. Having determined the values of resistance $R_{ab}$, $R_{bc}$ and $R_{ac}$, the corresponding values of conductivity $\sigma_{ab}$, $\sigma_{bc}$ and $\sigma_{ac}$ can be determined by dividing the cell constants $R_{ab}$, $R_{bc}$ and $R_{ac}$ by the respective values of soil resistance $R_{ab}$, $R_{bc}$ and $R_{ac}$. In a typical measurement, the values of $R_{ab}$, $R_{bc}$ and $R_{ac}$ were 115, 117 and 231, respectively, and the values of $R_{ab}$, $R_{bc}$ and $R_{ac}$ were 23180 ohms, 24913 ohms and 45060 ohms respectively. Solving for the conductivity $\sigma_{ab} = k_{ab}'/R_{ab} = 115/23180 = 0.0056$ mho per meter
$\sigma_{bc} = k_{bc}'/R_{bc} = 117/24913 = 0.0052$ mho per meter
and
$\sigma_{ac} = k_{ac}'/R_{ac} = 231/45060 = 0.0054$ mho meter.

The average or mean value of the conductivity of the soil then is $.0056 + .0052 + .0054/3 = 5.4$ millimhos per meter.

It will be noted that, although the length of the soil sample between probes 20a and 20c is substantially twice that of the soil sample between probes 20a and 20b and the soil sample between probes 20b and 20c, the constant $k$ of the cell for the probe pairs 20a and 20c is approximately twice that for the probes 20a and 20b and for 20b and 20c, so that the calculation for conductivity of the sample between electrodes 20a and 20c is not affected.

By making measurements of different portions of the soil, one can compensate for inherent lack of homogeneity of the soil and arrive at a meaningful average reading. This multiple measure also has a diagnostic value, since a reading which differs markedly from other readings indicates either a badly packed sample or a faulty contact between the soil sample and a probe, such as an airhole.

In order to avoid the effect of polarization of probes which occurs because of a low frequency chemical reaction at the boundary between the soil and the probes occurring between salts and acids in the soil and the metal probes, the soil is tested at an audio frequency of at least 1.5KHz which is in excess of this low frequency reaction. In practice, a frequency of 3KHz has been found satisfactory, although frequencies from about 1.5KHz to 10KHz have resulted in the absence of this undesirable chemical reaction. At a frequency of approximately 200Hz or less, the measured resistance of the soil climbs over a period of time, indicating the presence of the chemical potential owing to the galvanic action between the probes and certain constituents of the soil mentioned above. At a frequency of about 1.5KHz or greater, the effect of this phenomenon becomes negligible and accuracy of measurement is no longer impaired. It should be noted, however, that undesirable effects will occur if the frequency is too high; for example, at microwave frequencies, various high frequency affects come into play, such as skin effect and the need for some type of guiding mechanism for the energy.

Another factor in reducing the undesirable interaction mentioned above is the use of probes which are made of a material such as platinum or rhodium which are inert to the salts and acids in the soil or to a material which is heavily plated with such a material. In one application, the contact probes or electrodes were made of heavily plated rhodium over nickel on a ⅛ inch brass rod buffed to a hard finish before final assembly.

Obviously many other modifications and variations of the present invention are possible in the light of the above teachings. It is therefore to be understood that within the scope of the appended claims, the invention may be practiced otherwise then as specifically described.

What is claimed is:

1. A method for determining the conductivity of a soil sample adapted to be confined within a closed cell having chemically inert electrodes projecting into a soil-containing portion within said cell comprising the steps of;

filling said portion of said cell with a solution of known conductivity and measuring the resistance between said electrodes, obtaining the constant of said cell by multiplying said known conductivity and the measured resistance of said solution between said electrodes, replacing said solution with said sample of soil to be tested, connecting said electrodes into a resistance measuring bridge circuit, supplying said bridge circuit with a current of unknown magnitude and of frequency between 1.5kHz and 10kHz, balancing said bridge circuit to measure the resistance of said sample of soil between said electrodes; and determining the conductivity of the soil between said electrodes as the ratio of the aforesaid constant of said cell and the measured resistance of the soil between said electrodes.

2. Apparatus for determining the conductivity of a soil sample comprising a calibrated fluid-tight cell filled with a sample of soil to be analyzed, a pair of electrodes chemically inert to salts and acids within said soil, said electrodes projecting into a soil containing portion within said cell and connectable externally of said cell, a resistance measuring bridge circuit, and means for connecting said soil electrodes into a portion of said bridge circuit, said bridge circuit including a current supply of unknown magnitude and a frequency between 1.5 kHz and 10 kHz.

* * * * *